United States Patent [19]
Venegas

[11] Patent Number: 5,026,348
[45] Date of Patent: Jun. 25, 1991

[54] APPARATUS AND METHOD FOR THE DETECTION OF IV CATHETER OBSTRUCTION AND EXTRAVASATION

[75] Inventor: Jose G. Venegas, Nahant, Mass.

[73] Assignee: The General Hospital Corporation, Boston, Mass.

[21] Appl. No.: 203,280

[22] Filed: Jun. 6, 1988

[51] Int. Cl.$^5$ .................. A61M 5/00; G08B 21/00
[52] U.S. Cl. ................................ 604/122; 604/65; 128/DIG. 13; 73/19.01; 73/19.03
[58] Field of Search ................. 604/65-67, 604/118, 122, 123; 128/DIG. 12, DIG. 13; 73/19, 61 R, 19.03; 340/606, 608, 611; 361/285

[56] References Cited

U.S. PATENT DOCUMENTS

| | | | |
|---|---|---|---|
| 3,283,562 | 11/1966 | Heisig et al. | 73/19 |
| 3,898,637 | 8/1975 | Wolstenholme | 604/123 |
| 3,974,681 | 8/1976 | Namery | 128/DIG. 13 |
| 4,014,206 | 3/1977 | Taylor | 604/122 |
| 4,015,464 | 4/1977 | Miller et al. | 73/61 R |
| 4,068,521 | 1/1978 | Cosentino et al. | 73/19 |
| 4,122,713 | 10/1978 | Stasz et al. | 73/19 |
| 4,137,913 | 2/1979 | Georgi | 128/DIG. 12 |
| 4,256,437 | 3/1981 | Brolon | 604/123 |
| 4,418,565 | 12/1983 | St. John | 73/19 |
| 4,607,520 | 8/1986 | Dam | 73/19 |
| 4,648,869 | 3/1987 | Bobo, Jr. | 604/67 |
| 4,673,927 | 6/1987 | Cianciavicchia et al. | 604/65 |
| 4,778,451 | 10/1988 | Kamen | 128/DIG. 13 |
| 4,821,558 | 4/1989 | Pastrone et al. | 73/19 |
| 4,826,482 | 5/1989 | Kamen | 128/DIG. 13 |

FOREIGN PATENT DOCUMENTS

| | | | |
|---|---|---|---|
| 0838552 | 6/1981 | U.S.S.R. | 73/19 |
| 1196751 | 12/1985 | U.S.S.R. | 73/19 |

Primary Examiner—Stephen C. Pellegrino
Assistant Examiner—Ralph A. Lewis
Attorney, Agent, or Firm—Weingarten, Schurgin, Gagnebin & Hayes

[57] ABSTRACT

An in-line fluid conduit condition analyzer which includes a chamber placed in the conduit flow path and having one wall forming a piezoceramic bender that varies the chamber volume (or pressure) according to a predetermined waveform or noise spectrum and an associated piezoceramic pressure or displacement sensor. The time derivative of the displacement or the pressure are analyzed under computer control to identify conduit abnormalities. In particular application to intravenous fluid administration to patients, the system is capable of distinguishing a number of abnormalities including cathether obstruction, catheter needle out of the vein, catheter needle into the vein, as well as fluid bubble presence or conduit disconnection.

36 Claims, 4 Drawing Sheets

APPARATUS AND METHOD FOR THE DETECTION OF IV CATHETER OBSTRUCTION AND EXTRAVASATION

FIELD AND BACKGROUND OF THE INVENTION

The present invention relates to fluid injection systems and the detection of abnormalities in fluid injection conduits.

In the area of patient intravenous fluid injection, a catheter and needle are typically placed into a patient vein with the needle tip aperture located within the vein so as to permit infusion of the applied medication. In typical usage, the IV infusion is set up and left to operate for extended periods without attendance. In this condition it is important to be able to detect the presence of abnormalities in the fluid delivery system. More important to the safe and proper use of the infusion system is the ability to distinguish several possible abnormalities one from the other.

Additionally there are applications for insertion of catheters and associated instrumentation into patient veins for placement up or down the vein to locations such as heart cavities or elsewhere for more direct detection or treatment. In such cases it is important to be able to monitor the progress of the catheter to determine whether it progresses up the vein correctly or is encountering various difficulties along the way such as kinking, clotting, sticking on a vein wall, and to know which of the difficulties is being encountered.

In one embodiment for a catheter condition detection in the prior art as represented by U.S. Pat. No. 4,710,163, there is shown a system in which an infusion pump is modulated to produce a flow variation that is used to detect a blockage. Such a system adds great complexity to the pump, fails to provide a range of abnormalities that can be independently detected, and limits flexibility to the only situations where that pump can be used.

SUMMARY OF THE INVENTION

According to the teaching of the present invention, a fluid flow abnormality detection system is disclosed in which the condition of a fluid flow path, such as a catheter in patient applications or other fluid administration uses, is determined and the nature of any abnormality is revealed.

The detection system typically includes a fluid chamber inserted into the flow path independently of any pump or flow source. The chamber has a volume or force modulator and a displacement or pressure detector. The modulator typically includes a piezoelectric (piezoceramic typically) bender and corresponding sensor for bender displacement or chamber pressure variation. The bender is typically excited with one or a plurality of frequencies (band limited white noise for example) to superimpose the modulation signal onto the fluid in the flow path independently of the simultaneous pumping of the fluid through the system, if any.

The displacement or pressure is detected and the resulting signal sampled at plural points over a cycle and stored over several cycles of the modulating frequency for analysis. The displacement signal is time differentiated and the resulting derivative is a representation of the oscillatory modulation component of flow. Analysis of the signal includes several options including comparison of the mean of the square of individual cycle signal components to a standard, form fitting of the detected waveform to a model of fluid system dynamics that includes terms representing flow blockage, conduit moving out of a vein, into a vein, and conduit disconnection or air bubbles. The output reveals a change in any of the several parameters that reflect these conditions so that their onset or termination can be detected.

The use of a separate chamber that can be inserted in the flow path and that operates independently of any fluid flow provides greater flexibility and simplicity while at the same time permits detection of many abnormalities.

DESCRIPTION OF THE DRAWINGS

These and other features of the present invention are more fully set forth in the solely exemplary detailed description to follow and in the accompanying drawing of which.

DETAILED DESCRIPTION

The present invention contemplates the detection of fluid flow conduit condition aberrations or abnormalities by applying to the fluid a modulation on the flow by varying the volume in a chamber in the flow path and sensing the volume or pressure change that results over several cycles of applied modulation and analyzing the resulting detection signal for the presence of one of several possible anomalies.

Figure 1:
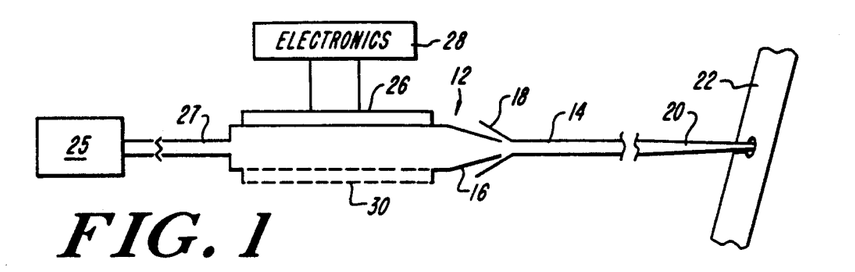
FIG. 1 is a diagram of the application of the invention to a fluid flow environment.

The general features of the invention are best illustrated by reference to FIG. 1 showing a fluid flow chamber 12 which is inserted into a flow path comprising a tube 14 via respective male and female couplings 16 and 18 of the chamber outlet and catheter inlet. Typically the tube 14 will communicate with an intravenous catheter or needle 20 that is to be inserted into a patient vein 22 or the catheter is to be inserted with any associated instrumentation through the vein 22 to a site for the administration of medication or other substance or detection is to occur. The chamber 12 includes an inlet conduit 27 for the application of the fluid from a syringe, separate pump, IV bottle or other source 25 under pressure that may be regular, irregular or otherwise. The inlet conduit 27 has a higher fluid impedance than tube 14 and catheter 20, by having a sufficiently long, narrow, and/or stiff passage, so that upstream effects do not interfere with detection of fluid path conditions in the chamber or tube 14 with catheter 20.

The chamber has on one wall a bender 26 which is deflected under the control of electronics 28 to cause the volume of the chamber 12 to vary accordingly. The fluid reaction to the volume modulation is sensed either by a displacement sensor associated with the bender 26 or a pressure transducer 30 forming another wall of the chamber 12. The sensed displacement or pressure is provided to the electronics 28 for analysis as described below.

Typically the drive applied to the bender 26 is a single frequency or multiple frequencies such as white noise in the range of frequencies above the normal body motional frequencies for noise separation and low enough for the parameters to be detected to respond to it, typically 5–50 Hz. Among the parameters to be sensed and distinguished from each other are the clogging of the conduit, penetration of the needle into soft body tissue or the vein 22, the placement of the needle in the cavity of the vein 22, or the existence of an air bubble or conduit rupture or disconnection.

Figure 2:
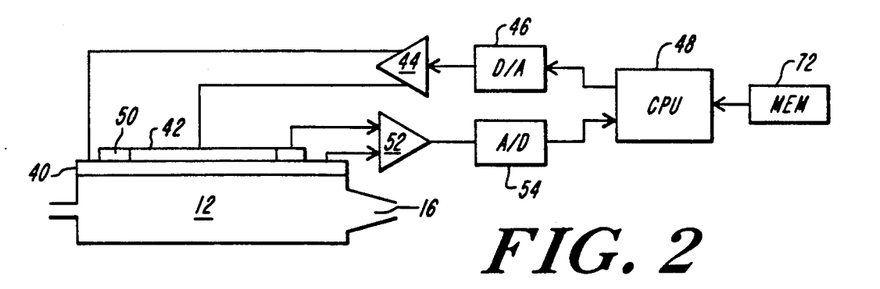
FIG. 2 is a circuit and structure diagram illustrating one embodiment of the present invention.

In FIG. 2, the embodiment of the invention for use with a displacement sensor is illustrated. As shown there the bender comprises a conductive plate 40 such as brass on which a piezoceramic crystal 42 is centered to act as deflector for the plate 40 in response to excitation from a driver amplifier 44. The excitation causes the crystal 42 to shrink or expand which induces a deflection in resilient plate 40. The crystal excitation to amplifier 44 is applied through a digital-to-analog converter 46 in digital increments generated by a computer 48 corresponding to single or multiple frequencies.

Figure 3A:
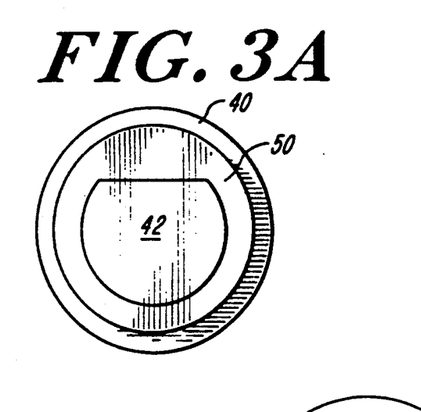
FIGS. 3A, 3B and 3C illustrate bender and displacement detectors according to the present invention.
Figure 3B:
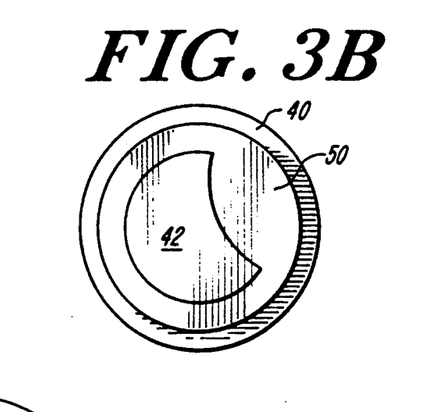
Figure 3C:
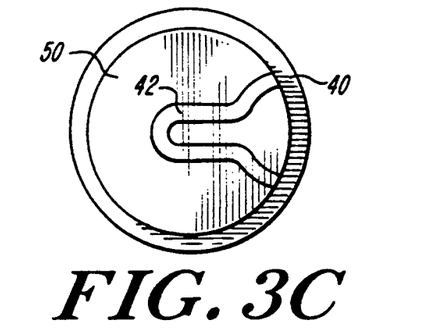

The bender includes a section of separate piezoelectric ceramic crystal 50 which may surround the deflection crystal 42 as shown in FIG. 3A or have a particularly tailored shape as shown in FIGS. 3B–3C. The piezoelectric voltage induced by the deflection of the brass plate 40 is coupled through a buffer amplifier 52 and an analog-to-digital converter 54 to the computer 48 where they are sampled several times per cycle in order to obtain phase information and over several cycles to insure capture of representative response sampling. The processing of the sampled signal is shown below.

Figure 4:
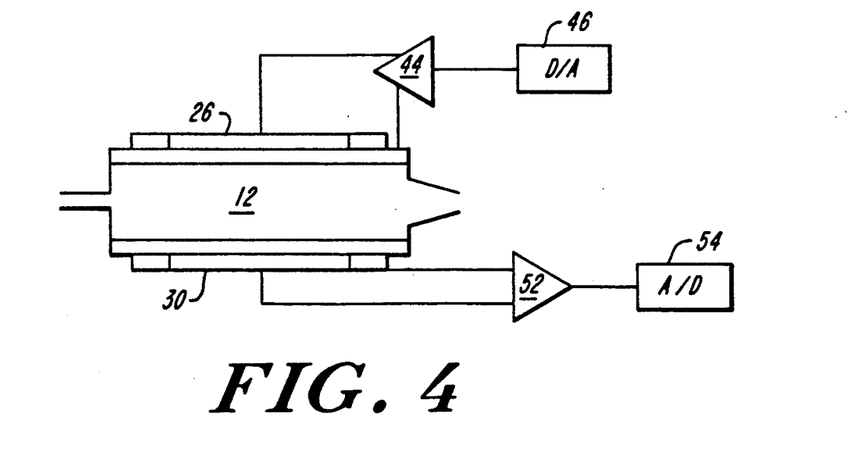
FIG. 4 illustrates circuitry and structure according to a second embodiment of the invention.

In the case where the fluid response to the bender excitation is sensed as a pressure, the embodiment of FIG. 4 is alternatively or additionally used. The driver amplifier 44 couples to the bender 26 and the sensor piezoelectric crystal 30 output is applied to the buffer 52 and converter 54 as described above.

Figure 5:
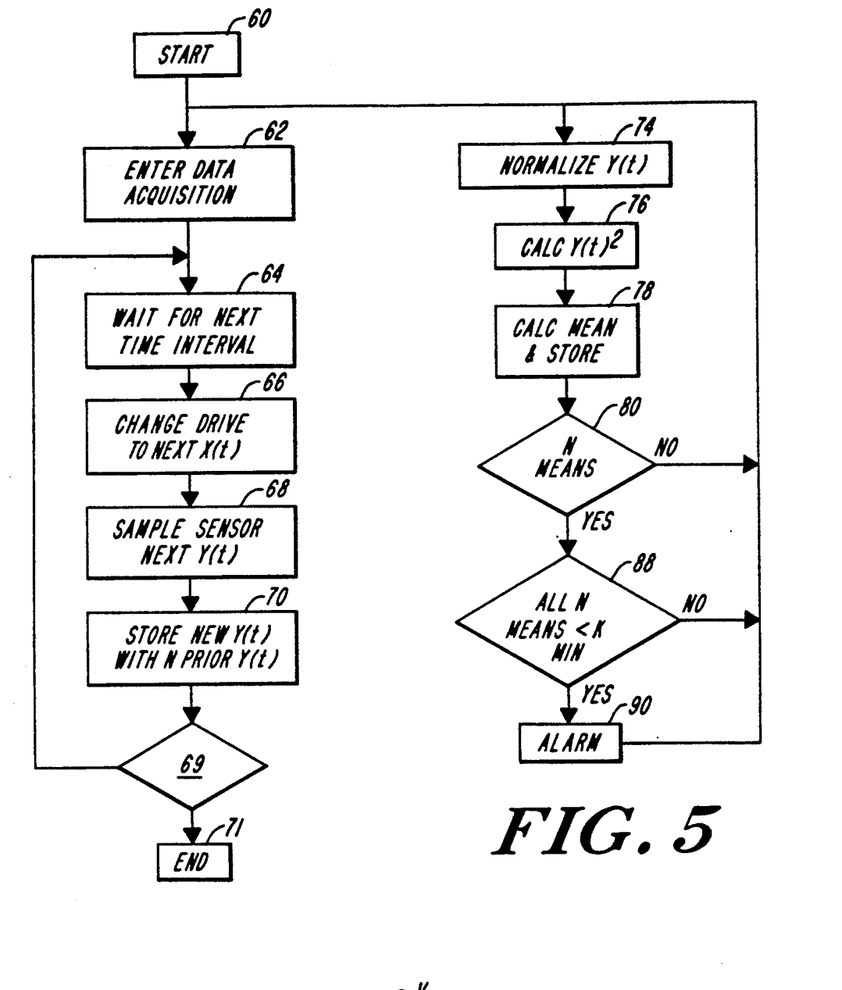
FIG. 5 is a flow chart illustrating excitation, sensing and data analysis according to one data analysis embodiment of the invention.

The computer 48 is programmed according to the flow chart of FIG. 5. From a start state 60 processing proceeds along parallel paths for data acquisition and analysis respectively. The data acquisition path includes a step 62 which activates the acquisition processing and proceeds to a step 64 which includes a timer to regulate the intervals between the generation of each byte of drive signal. The next step 66 proceeds to generate the next digital value in the series of small increments repeatedly stepped through in the plural step digitization of the values of one cycle of a single frequency signal in a steady state reproduction of that signal or the digital values of a random or white noise signal, band limited to the frequency range of 5–50 Hz.

In step 68 the sensor data, $Y(t)$, for either displacement or pressure transducers (as explained below), is taken for the corresponding excitation signal, $X(t)$. In step 70 this data point is stored along with the prior $N \times M$ data points in a memory 72 associated with the computer 48. The value of $N \times M$ is selected so as to preserve in memory sensed data corresponding to $M$ data points in each of $N$, (several ~ 10) cycles of excitation. From the step 70 processing returns to step 64 to repeat the entire set of steps indexed one more step forward in time in the cycle of excitation signals, or the system exits if processing is complete through step 69 to step 71.

Figure 6:
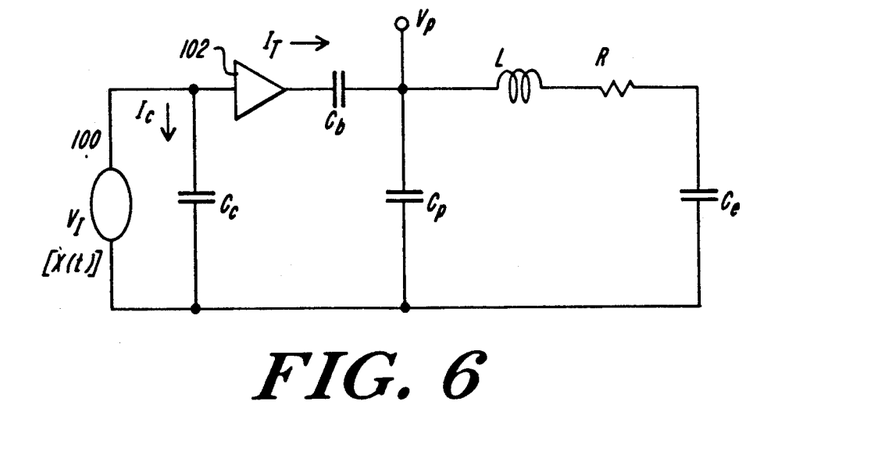
FIG. 6 is a circuit diagram illustrating a circuit equivalent data analysis embodiment of the present invention.

The data processing flow chart, which can operate asynchronously with respect to the data acquisition processing, includes a step 74 in which the $N \times M$ data points are normalized by subtracting a leakage term described below with respect to FIG. 6 that effectively removes Ic. In subsequent step 76 each $M$ data point in a cycle is squared to permit an analysis based on RMS levels and in the next step 78 the squared values for all the $M$ points in the cycle are averaged. In step 80 the decision is made as to whether all $N$ cycles have been processed and processing continues through steps 74–80 until that has been achieved. At that point the processing continues to an abnormality detection step 88 which compares the $N$ means against a preset value to test the values for being out of range indicating a blockage. If no blockage is found as represented by all $N$ means not being less than a value "K" determined in step 88 processing continues back to step 74. The $N$ means being below "K" in step 88 causes the system, in step 90, to activate an alarm and continue back to step 74.

For the evaluation of the nature of a fluid flow path abnormality, an analysis of the displacement or pressure response of the chamber 12 based on an electrical circuit equivalent is used. The circuit of FIG. 6 presents this equivalent in which a voltage source 100 represents the excitation to the bender 26. A leakage current Ic through a shunt capacitance Cc corresponds to a direct coupling between the input and output. This can be calibrated out of the data by measuring Ic as the response to the system with blocked chamber inlets and outlets and then subtracting that value from each data point in step 74. The value of the circuit current It, through the remainder of the circuit, proceeds through an inverter 102 (provided to permit flow and voltage directions to be the same) and a capacitance Cb corresponding to the bender's response characteristics, such as elasticity, and can be found for the system by the response of the system in air after the leakage current Ic is subtracted. A shunt capacitance Cp corresponds to the compliance of the chamber and conduit and any air bubbles. Series Inductor L and resistor R represent respectively the inertia of the fluid column within the catheter, and the pressure dissipation due to viscous effects along the catheter, and to effects such as blockage, clots, etc. at the exit of the fluid column. The return path is provided through a capacitance Ce which corresponds to the compliance of the space beyond the tip of the catheter or needle such as tissue or interstitial space of vein lumen.

Figure 7:
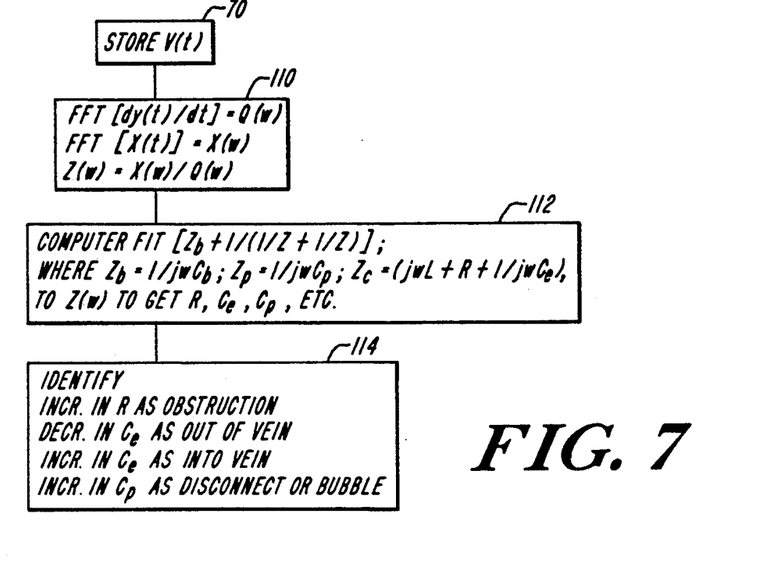
FIG. 7 is a flow chart illustrating multiple condition analysis for displacement detection according to the invention.

To analyze the fluid flow path fully, reliance is placed upon this equivalent circuit and the model equation that represents it and the sensor data is fit to that model to obtain the values or changes in the circuit elements R, Ce, and Cp and thus the fluid equivalents to them. In the case of the displacement sensor and a white noise or multifrequency drive to the bender in the typical range of 5–50 Hz, FIG. 7 represents the signal processing on assembled data Y(t) corresponding to the integral of $I_T$ in FIG. 6. That data is differentiated digitally within the computer and the fast Fourier transform taken of that derivative along with the excitation signal in step 110. In a subsequent step 112 the ratio of that transformed data, an impedance equivalent to the combined system impedances as seen by the excitation voltage is fit to the model equation using the relationships shown in that step and known computerized data fitting algorithms. From this fit or regression analysis, values for R, Ce, and Cp are obtained. Subsequent step provides an output indication from the computer 48 of changes in these and in particular provides an indication of an increasing obstruction from an increase in R, an increase or decrease in Ce as the catheter moving into or out of a compliant space such as into a vein or into the tissue around a vein, and an increase in Cp as a conduit disconnection or air bubble.

Figure 8:
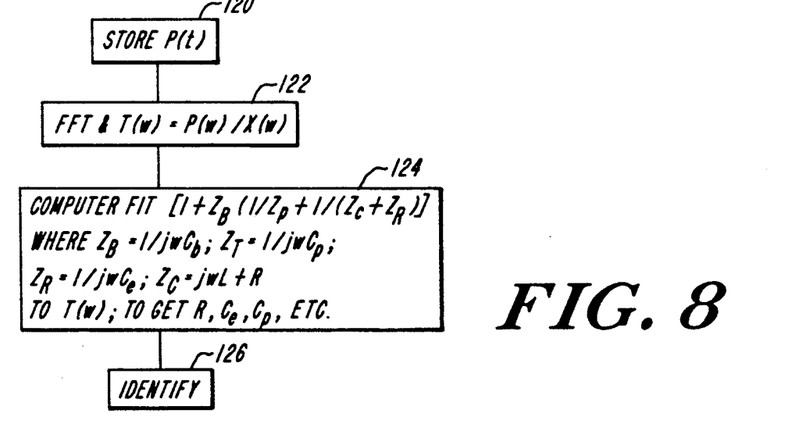
FIG. 8 is a flow chart illustrating multiple condition analysis for pressure sensing according to the invention.

In the case of pressure detection, FIG. 8 shows the processing for the same drive excitation of band limited white noise or multiple frequencies. Pressure data is collected for a time period corresponding to several cycles of the lowest frequency in the drive excitation at a rate of at least twice the highest frequency in the drive excitation. The pressure (corresponding to $V_p$ of FIG. 6) and excitation data is fast Fourier transformed as before and the ratio is fit to the model equation in sequential steps 122 and 124. In step 124 values for R, Ce, and Cp are obtained from the regression analysis and in step 126 an output indication of the fluid flow path characteristics is provided from these values as described before.

The system just described and the several embodiments permit complete monitoring of the condition of a fluid flow path such as an IV infusion system to identify which of the several possible abnormalities is encountered. The sensitivity and selectively of this system also permits more intelligent guiding of a catheter system through a vein to a site of medication or detection.

Figure 9:
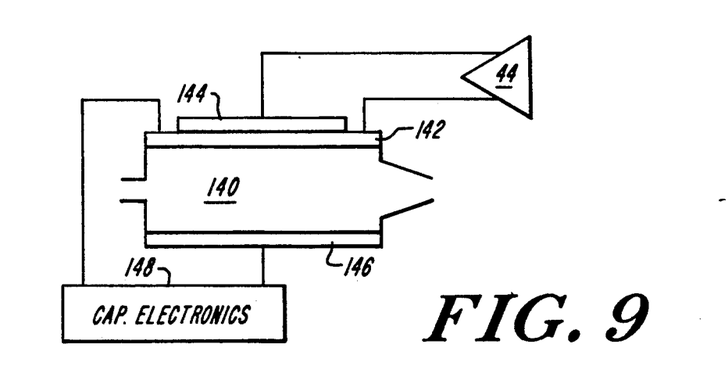
FIG. 9 is a chamber diagram utilizing capacitive sensing.

FIG. 9 shows a first modification of the present invention in which the chamber of FIG. 4 is modified to provide a chamber 140 having a bender formed by a plate 142 and crystal 144 on one side, and a plate 146 on the other side of the chamber. The crystal 144 is excited from the amplifier 44 as noted above. A capacitor is formed by the plates 142 and 146 and each is connected to capacitive processing electronics 148 which provides an output signal corresponding to the capacitance, and thus distance, between the plates 142 and 146. This signal is used in place of the signal from the crystal portion 52 in FIG. 2 as an indication of volume change.

The capacitive sensing of volume variation in FIG. 9 is particularly sensitive to bubble presence in the chamber 140 which would affect the dielectric constant of the fluid in the chamber.

Figure 10:
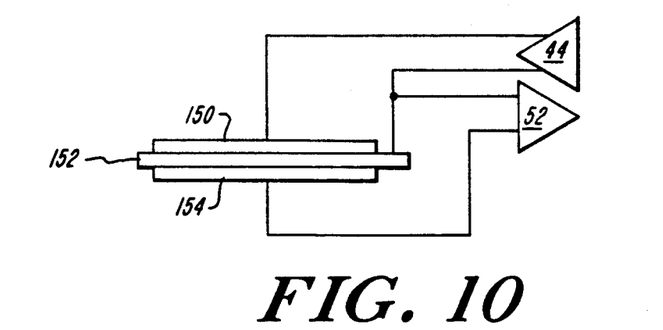
FIG. 10 is a diagram of a modified bender having ceramic crystals on opposing sides.

The bender in the view of FIG. 10 has been modified to include a crystal 150 on the top side of a plate 152 along with a crystal 154, or any material with an electrical sensitivity to tension and compression, on the bottom and opposite side of the plate 152. The bender formed between the crystal 150 and plate 152 is driven by excitation from the amplifier 44 as above. The response of the bender is provided by applying the signal from the bottom crystal 154 to the output amplifier 52.

The design of the bender in FIG. 10 has the advantage of eliminating the leakage represented by the leakage capacitance Cc.

The above described invention is capable of practice in various other embodiments; and accordingly, the invention is intended to be limited only by the scope of the following claims.

I claim:

1. An in-line fluid conduit condition analyzer comprising
    a chamber adapted for insertion in the flow path of a fluid conduit;
    means for varying the volume of the chamber in response to a predetermined drive signal;
    means for sensing a variation in volume or pressure in said chamber in response to the variation in volume produced by said drive signal, said sensing means including a capacitive sensor having first and second capacitor plates, one of which is a part of said varying means; and
    means for independently detecting each of a set of abnormalities in the flow path in response to the sensed variation.

2. An in-line fluid conduit condition analyzer comprising:
    a chamber adapted for insertion in the flow path of a fluid conduit;
    means for varying the volume of the chamber in response to a predetermined drive signal;
    means for sensing a variation in volume of said chamber in response to said drive signal, said sensing means including a capacitive sensor having first and second capacitor plates, one of which is a part of said varying means; and
    means for detecting an abnormality in the flow path in response to the sensed variation.

3. An in-line fluid conduit condition analyzer comprising:
    a chamber adapted for insertion in the flow path of a fluid conduit;
    means for varying the volume of the chamber in response to a predetermined multicycle single frequency drive signal;
    means for sensing a variation in a condition within said chamber in response to said drive signal, said sensing means including a capacitive sensor having first and second capacitor plates, one of which is a part of said varying means; and
    means for detecting an abnormality in the flow path in response to the sensed variation.

4. An in-line conduit condition analyzer comprising:
    a chamber adapted for insertion in the flow path of a fluid conduit;
    means for varying the volume of the chamber according to a predetermined multi-frequency drive signal;
    means for sensing a variation in a condition of a fluid in said chamber in response to the variation in volume produced by said drive signal, said sensing means including a capacitive sensor having first and second capacitor plates, one of which is a part of said varying means; and
    means for detecting an abnormality in the flow path in response to the sensed variation.

5. An in-line fluid conduit condition analyzer comprising:
    a chamber adapted for insertion in the flow path of a fluid conduit;
    means for varying a condition of a fluid from said conduit in said chamber according to a predetermined drive signal;

means for sensing a change in a fluid parameter associated with said chamber in response to the variation in condition produced by said drive signal, said sensing means including a capacitive sensor having first and second capacitor plates, one of which is a part of said varying means; and means for independently detecting each of a plurality of abnormalities in the flow path in response to the sensed change.

6. An in line fluid conduit analyzer comprising:

a chamber adapted for insertion in the flow path of a fluid conduit to be filled with fluid thereby;

means for applying a force to the fluid in the chamber in response to a predetermined drive signal;

means for sensing a variation in pressure in said chamber in response to the force applied to the fluid in said chamber produced by said drive signal, said sensing means including a capacitive sensor having first and second capacitor plates, one of which is a part of said varying means; and means for independently detecting each of a set of abnormalities in the flow path in response to the sensed variation.

7. An in-line fluid conduit condition analyzer comprising a chamber adapted for insertion in the flow path of a fluid conduit;

means for varying the volume of the chamber in response to a predetermined drive signal;

means for sensing a variation in volume or pressure in said chamber in response to the variation in volume produced by said drive signal;

said varying and sensing means including a common plate and a respective electric-mechanical motivator and sensor affixed to opposite sides of said plate; and means for independently detecting each of a set of abnormalities in the flow path in response to the sensed variation.

8. An in-line fluid conduit condition analyzer comprising:

a chamber adapted for insertion in the flow path of a fluid conduit;

means for varying the volume of the chamber in response to a predetermined drive signal;

means for sensing a variation in volume of said chamber in response to said drive signal;

said varying and sensing means including a common plate and a respective electric-mechanical motivator and sensor affixed to opposite sides of said plate; and means for detecting an abnormality in the flow path in response to the sensed variation.

9. An in-line fluid conduit condition analyzer comprising:

a chamber adapted for insertion in the flow path of a fluid conduit;

means for varying the volume of the chamber in response to a predetermined multicycle single frequency drive signal;

means for sensing a variation in a condition within said chamber in response to said drive signal;

said varying and sensing means including a common plate and a respective electric-mechanical motivator and sensor affixed to opposite sides of said plate; and means for detecting an abnormality in the flow path in response to the sensed variation.

10. An in-line fluid conduit condition analyzer comprising:

a chamber adapted for insertion in the flow path of a fluid conduit;

means for varying the volume of the chamber according to a predetermined multi-frequency drive signal;

means for sensing a variation in a condition of a fluid in said chamber in response to the variation in volume produced by said drive signal;

said varying and sensing means including a common plate and a respective electric-mechanical motivator and sensor affixed to opposite sides of said plate; and means for detecting an abnormality in the flow path in response to the sensed variation.

11. An in-line fluid conduit condition analyzer comprising:

a chamber adapted for insertion in the flow path of a fluid conduit;

means for varying a condition of a fluid from said conduit in said chamber according to a predetermined drive signal;

means for sensing a change in a fluid parameter associated with said chamber in response to the variation in condition produced by said drive signal;

said varying and sensing means including a common plate and a respective electric-mechanical motivator and sensor affixed to opposite sides of said plate; and means for independently detecting each of a plurality of abnormalities in the flow path in response to the sensed change.

12. An in line fluid conduit analyzer comprising:

a chamber adapted for insertion in the flow path of a fluid conduit to be filled with fluid thereby;

means for applying a force to the fluid in the chamber in response to a predetermined drive signal;

means for sensing a variation in pressure in said chamber in response to the force applied to the fluid in said chamber produced by said drive signal;

said varying and sensing means including a common plate and a respective electric-mechanical motivator and sensor affixed to opposite sides of said plate; and means for independently detecting each of a set of abnormalities in the flow path in response to the sensed variation.

13. An in-line fluid conduit condition analyzer for use in a fluid flow path that includes a fluid conduit, comprising:

a chamber having a volume and configured for insertion in the fluid flow path of the fluid conduit;

means for generating a predetermined low frequency drive signal;

a bender for varying said volume of said chamber in response to said predetermined low frequency drive signal wherein fluid flowing through said chamber is modulated by said predetermined low frequency drive signal;

means for sensing variations in pressure in said chamber in response to said modulated fluid flowing therethrough; and means for detecting and distinguishing each of a set of abnormalities in the fluid flow path in response to sensed variations in pressure of said chamber.

14. An in-line fluid conduit condition analyzer for use in a fluid flow path that includes a fluid conduit, comprising:
 a chamber having a volume and configured for insertion in the fluid flow path of the fluid conduit;
 means for generating a predetermined low frequency drive signal;
 a bender for varying said volume of said chamber in response to said predetermined low frequency drive signal wherein fluid flowing through said chamber is modulated by said low frequency predetermined drive signal;
 means for sensing variations in volume in said chamber in response to said modulated fluid flowing therethrough; and
 means for detecting and distinguishing each of a set of abnormalities in the fluid flow path in response to sensed variations in volume in said chamber.

15. An in-line fluid conduit condition analyzer for use in a fluid flow path that includes a fluid conduit, comprising:
 a chamber having a volume and configured for insertion in the fluid flow path of the fluid conduit;
 means for generating a predetermined multicycle single low frequency drive signal;
 a bender for varying said volume in said chamber in response to said predetermined multicycle single low frequency drive signal wherein fluid flowing through said chamber is modulated by said predetermined multicycle single low frequency drive signal;
 means for sensing variations in a condition of said chamber in response to said modulated fluid flowing therethrough; and
 means for detecting and distinguishing each of a set of abnormalities in the fluid flow path in response to sensed variations in said condition in said chamber.

16. An in-line fluid conduit condition analyzer for use in a fluid flow path that includes a fluid conduit, comprising:
 a chamber having a volume and configured for insertion in the fluid flow path of the fluid conduit;
 means for generating a predetermined low multi-frequency drive signal;
 a bender for varying said volume of said chamber according to said predetermined low multi-frequency drive signal wherein fluid flowing through said chamber is modulated by said predetermined low multi-frequency drive signal;
 means for sensing variations in a condition of said modulated fluid flowing through said chamber;
 means for detecting and distinguishing each of a set of abnormalities in the fluid flow path in response to sensed variations in said condition in said modulated fluid flowing through said chamber.

17. An in-line fluid condition analyzer for use in a fluid flow path that includes a fluid conduit, comprising:
 a chamber having a volume and configured for insertion in the fluid flow path of the fluid conduit;
 means for generating a predetermined low frequency drive signal;
 a bender for varying a condition of a fluid flowing through said chamber according to said predetermined low frequency drive signal wherein said fluid flowing through said chamber is modulated by said predetermined low frequency drive signal;
 means for sensing changes in a fluid parameter associated with said modulated fluid flowing through said chamber;
 means for independently detecting and distinguishing each of a plurality of abnormalities in the fluid flow path in response to sensed changes in said fluid parameter of said modulated fluid flowing through said chamber.

18. An in-line fluid conduit analyzer for use in a fluid flow path that includes a fluid conduit, comprising:
 a chamber configured for insertion in the fluid flow path of the fluid conduit such that fluid flows through said chamber;
 means for generating a predetermined low frequency drive signal;
 a bender for applying a force to the fluid flowing through said chamber wherein the fluid flowing through said chamber is modulated by said predetermined low frequency drive signal;
 means for sensing variations in pressure in said chamber in response to said modulated fluid flowing through said chamber;
 means for independently detecting and distinguishing each of a set of abnormalities in the fluid flow path in response to sensed variations in pressure in said chamber.

19. The analyzer of claims 13, 14, 15, 16, 17, or 18 wherein said bender includes:
 a conductive plate forming one wall of said chamber; and
 a piezoelectric crystal mounted in combination with said conductive plate.

20. An in-line fluid conduit condition analyzer for use in a fluid flow path that includes a fluid conduit, comprising:
 a chamber having a volume and configured for insertion in the fluid flow path of the fluid conduit;
 means for generating a predetermined low frequency drive signal;
 means for varying said volume of said chamber in response to said predetermined low frequency drive signal wherein fluid flowing through said chamber is modulated by said predetermined low frequency drive signal;
 a crystal detector for sensing variations in pressure in said chamber in response to said modulated fluid flowing therethrough; and
 means for detecting and distinguishing each of a set of abnormalities in the fluid flow path in response to sensed variations in pressure of said chamber.

21. An in-line fluid conduit condition analyzer for use in a fluid flow path that includes a fluid conduit, comprising;
 a chamber having a volume and configured for insertion in the fluid flow path of the fluid conduit.
 means for generating a predetermined low frequency drive signal;
 means for varying said volume of said chamber in response to said predetermined low frequency drive signal wherein fluid flowing through said chamber is modulated by said low frequency predetermined drive signal;
 a crystal detector for sensing variations in volume in said chamber in response to said modulated fluid flowing therethrough; and
 means for detecting and distinguishing each of a st of abnormalities in the fluid flow path in response to sensed variations in volume in said chamber.

22. An in-line fluid conduit condition analyzer for use in a fluid flow path that includes a fluid conduit, comprising:
- a chamber having a volume and configured for insertion in the fluid flow path of the fluid conduit;
- means for generating a predetermined multicycle single low frequency drive signal;
- means for varying said volume of said chamber in response to said predetermined multicycle single low frequency drive signal wherein fluid flowing through said chamber is modulated by said predetermined multicycle single low frequency drive signal;
- a crystal detector for sensing variations in a condition of said chamber in response to said modulated fluid flowing therethrough; and
- means for detecting and distinguishing each of a set of abnormalities in the fluid flow path in response to sensed variations in said condition in said chamber.

23. An in-line fluid conduit condition analyzer for use in a fluid flow path that includes a fluid conduit, comprising:
- a chamber having a volume and configured for insertion in the fluid flow path of the fluid conduit;
- means for generating a predetermined low multi-frequency drive signal;
- means for varying said volume of said chamber according to said predetermined low multi-frequency drive signal wherein fluid flowing through said chamber is modulated by said predetermined low multi-frequency drive signal;
- a crystal detector for sensing variations in a condition of said modulated fluid flowing through said chamber;
- means for detecting and distinguishing each of a set of abnormalities in the fluid flow path in response to sensed variations in said condition in said modulated fluid flowing through said chamber.

24. An in-line fluid conduit condition analyzer for use in a fluid flow path that includes a fluid conduit, comprising:
- a chamber having a volume and configured for insertion in the fluid flow path of the fluid conduit;
- means for generating a predetermined low frequency drive signal;
- means for varying a condition of a fluid flowing through said chamber according to said predetermined low frequency drive signal wherein said fluid flowing through said chamber is modulated by said predetermined low frequency drive signal;
- a crystal detector for sensing changes in a fluid parameter associated with said modulated fluid flowing through said chamber;
- means for independently detecting and distinguishing each of a plurality of abnormalities in the fluid flow path in response to sensed changes in said fluid parameter of said modulated fluid flowing through said chamber.

25. The analyzer of claims 20, 21, 22, 23 or 24 wherein said detector is a piezoelectric detector on a conductive plate forming a wall of said chamber.

26. The analyzer of claims 20, 21, 22, 23, or 24 wherein said detector and said means for varying share a common conductive plate.

27. An in-line fluid conduit analyzer for use in a fluid flow path that includes a fluid conduit, comprising:
- a chamber configured for insertion in the fluid flow path of the fluid conduit such that fluid flows through said chamber;
- means for generating a predetermined low frequency drive signal;
- means for applying a force to the fluid flowing through said chamber wherein the fluid flowing through said chamber is modulated by said predetermined low frequency drive signal;
- a crystal detector for sensing variations in pressure in said chamber in response to said modulated fluid flowing through said chamber;
- means for independently detecting and distinguishing each of a set of abnormalities in the fluid flow path in response to sensed variations in pressure in said chamber.

28. An in-line fluid conduit condition analyzer for use in a fluid flow path that includes a fluid conduit, comprising:
- a chamber having a volume and configured for insertion in the fluid flow path of the fluid conduit;
- means for generating a predetermined low frequency drive signal;
- means for varying said volume of said chamber in response to said predetermined low frequency drive signal wherein fluid flowing through said chamber is modulated by said predetermined low frequency drive signal;
- a capacitive sensor for sensing variations in pressure in said chamber in response to said modulated fluid flowing therethrough; and
- means for detecting and distinguishing each of a set of abnormalities in the fluid flow path in response to sensed variations in pressure of said chamber.

29. An in-line fluid conduit condition analyzer for use in a fluid flow path that includes a fluid conduit, comprising:
- a chamber having a volume and configured for insertion in the fluid flow path of the fluid conduit;
- means for generating a predetermined low frequency drive signal;
- means for varying said volume of said chamber in response to said predetermined low frequency drive signal wherein fluid flowing through said chamber is modulated by said low frequency predetermined drive signal;
- a capacitive sensor for sensing variations in volume in said chamber in response to said modulated fluid flowing therethrough; and
- means for detecting and distinguishing each of a set of abnormalities in the fluid flow path in response to sensed variations in volume in said chamber.

30. An in-line fluid conduit condition analyzer for use in a fluid flow path that includes a fluid conduit, comprising:
- a chamber having a volume and configured for insertion in the fluid flow path of the fluid conduit;
- means for generating a predetermined multicycle single low frequency drive signal;
- means for varying said chamber in response to said predetermined multicycle single low frequency drive signal wherein fluid flowing through said chamber is modulated by said predetermined multicycle single low frequency drive signal;
- a capacitive sensor for sensing variations in a condition of said chamber in response to said modulated fluid flowing therethrough; and means for detecting and distinguishing each of a set of abnormalities in the fluid flow path in response to sensed variations in said condition in said chamber.

31. An in-line fluid conduit condition analyzer for use in a fluid flow path that includes a fluid conduit, comprising:
a chamber having a volume and configured for insertion in the fluid flow path of the fluid conduit;
means for generating a predetermined low multi-frequency drive signal;
means for varying said volume of said chamber according to said predetermined low multi-frequency drive signal wherein fluid flowing through said chamber is modulated by said predetermined low multi-frequency drive signal;
a capacitive sensor for sensing variations in a condition of said modulated fluid flowing through said chamber;
means for detecting and distinguishing each of a set of abnormalities in the fluid flow path in response to sensed variations in said condition in said modulated fluid flowing through said chamber.

32. An in-line fluid conduit condition analyzer for use in a fluid flow path that includes a fluid conduit, comprising:
a chamber having a volume and configured for insertion in the fluid flow path of the fluid conduit;
means for generating a predetermined low frequency drive signal;
means for varying a condition of a fluid flowing through said chamber according to said predetermined low frequency drive signal wherein said fluid flowing through said chamber is modulated by said predetermined low frequency drive signal;
a capacitive sensor for sensing changes in a fluid parameter associated with said modulated fluid flowing through said chamber;
means for independently detecting and distinguishing each of a plurality of abnormalities in the fluid flow path in response to sensed changes in said fluid parameter of said modulated fluid flowing through said chamber.

33. An in-line fluid conduit analyzer for use in a fluid flow path that includes a fluid conduit, comprising:
a chamber configured for insertion in the fluid flow path of the fluid conduit such that fluid flows through said chamber;
means for generating a predetermined low frequency drive signal;
means for applying a force to the fluid flowing through said chamber wherein the fluid flowing through said chamber is modulated by said predetermined low frequency drive signal;
a capacitive sensor for sensing variations in pressure in said chamber in response to said modulated fluid flowing through said chamber;
means for independently detecting and distinguishing each of a set of abnormalities in the fluid flow path in response to sensed variations in pressure in said chamber.

34. The analyzer of claims 13–32 or 33 wherein the fluid conduit is a tube terminating in an intravenous catheter or a needle for patient vein insertion and said means for detecting and distinguishing includes means for detecting and distinguishing each abnormality from said set of abnormalities including conduit obstruction, conduit out of vein, conduit in vein, conduit disconnected and conduit bubble.

35. The analyzer of claims 14, 15, 21 or 22 wherein said means for detecting and distinguishing includes
means for finding the mean of the square of the sensed variations in plural, discrete, time sequential values; and
means for comparing said plural, discrete time sequential values of the means of the square of the sensed variations against a preset value to identify abnormalities in the fluid flow path.

36. The analyzer of claim 23 wherein said predetermined low multi-frequency drive signal generated by said means for varying is a white noise signal having an approximate bandwidth in the range of 5 to 50 Hz.

* * * * *

UNITED STATES PATENT AND TRADEMARK OFFICE
CERTIFICATE OF CORRECTION

PATENT NO. : 5,026,348

DATED : June 25, 1991

INVENTOR(S) : Jose G. Venegas

It is certified that error appears in the above-identified patent and that said Letters Patent is hereby corrected as shown below:

In the Abstract, line 12, "cathether" should read --catheter--.

Column 6, line 48, "An in-line conduit" should read --An in-line fluid conduit--.

Column 9, line 27, "a bender for varying said volume in" should read --a bender for varying said volume of--.

Column 9, line 57, "An in-line fluid condition" should read --An in-line fluid conduit condition--.

UNITED STATES PATENT AND TRADEMARK OFFICE
CERTIFICATE OF CORRECTION

PATENT NO. : 5,026,348

DATED : June 25, 1991

INVENTOR(S) : Jose G. Venegas

It is certified that error appears in the above-identified patent and that said Letters Patent is hereby corrected as shown below:

Column 10, line 55, "in the fluid flow path of the fluid conduit." should read --in the fluid flow path of the fluid conduit;--.

Column 10, line 66, "means for detecting and distinguishing each of a st" should read --means for detecting and distinguishing each of a set--.

Column 12, line 61, "means for varying said chamber in response to" should read --means for varying said volume of said chamber in response to--.

Signed and Sealed this

Ninth Day of March, 1993

Attest:

STEPHEN G. KUNIN

*Attesting Officer*     Acting Commissioner of Patents and Trademarks